(12) United States Patent
Essaddam

(10) Patent No.: US 10,640,442 B2
(45) Date of Patent: *May 5, 2020

(54) POLYETHYLENE TEREPHTHALATE DEPOLYMERIZATION

(71) Applicant: Loop Industries, Inc., Los Angeles, CA (US)

(72) Inventor: Hatem Essaddam, Ste. Therese (CA)

(73) Assignee: LOOP INDUSTRIES, INC., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/117,672

(22) Filed: Aug. 30, 2018

(65) Prior Publication Data

US 2018/0370894 A1    Dec. 27, 2018

Related U.S. Application Data

(63) Continuation of application No. 15/377,460, filed on Dec. 13, 2016, now Pat. No. 10,087,130, which is a continuation of application No. 14/795,116, filed on Jul. 9, 2015, now Pat. No. 9,550,713.

(51) Int. Cl.
*C07C 51/09* (2006.01)
*C07C 29/128* (2006.01)
*C08J 11/24* (2006.01)
*C07C 29/09* (2006.01)

(52) U.S. Cl.
CPC ............ *C07C 51/09* (2013.01); *C07C 29/095* (2013.01); *C07C 29/1285* (2013.01); *C08J 11/24* (2013.01); *C08J 2367/02* (2013.01); *C08J 2367/03* (2013.01)

(58) Field of Classification Search
None
See application file for complete search history.

(56) References Cited

U.S. PATENT DOCUMENTS

| | | |
|---|---|---|
| 3,501,420 A | 3/1970 | Stevenson et al. |
| 4,355,175 A | 10/1982 | Pusztaszeri |
| 5,045,122 A | 9/1991 | Tindall et al. |
| 5,051,528 A | 9/1991 | Naujokas et al. |
| 5,236,959 A | 8/1993 | Oakley et al. |
| 5,328,982 A | 7/1994 | Tindall et al. |
| 5,386,055 A | 1/1995 | Lee et al. |
| 5,668,186 A | 9/1997 | Brunelle et al. |
| 6,528,546 B2 | 3/2003 | Lee et al. |
| 6,670,503 B2 | 12/2003 | Broccatelli |
| 6,706,843 B1 | 3/2004 | Ishihara et al. |
| 6,720,448 B2 | 4/2004 | Broccatelli |
| 6,911,546 B2 | 6/2005 | Hedrick et al. |
| 6,916,936 B2 | 7/2005 | Hedrick et al. |
| 7,053,221 B2 | 5/2006 | Hedrick et al. |
| 7,462,649 B2 | 12/2008 | Nakao et al. |
| 7,544,800 B2 | 6/2009 | Hedrick et al. |
| 7,750,057 B2 | 7/2010 | Ogasawara |
| 8,309,618 B2 | 11/2012 | Hedrick et al. |
| 8,492,504 B2 | 7/2013 | Hedrick et al. |
| 8,513,379 B2 | 8/2013 | Matsumura |
| 9,550,713 B1 | 1/2017 | Essaddam |
| 10,087,130 B2 | 10/2018 | Essaddam |
| 10,252,976 B1* | 4/2019 | Essaddam ............. C07C 29/095 |
| 2008/0242751 A1 | 10/2008 | Kurian et al. |
| 2009/0032015 A1 | 2/2009 | Myllymaki et al. |
| 2009/0171113 A1 | 7/2009 | Anderson et al. |
| 2009/0318579 A1 | 12/2009 | Ikenaga |
| 2011/0004014 A1 | 1/2011 | Hedrick et al. |
| 2013/0345453 A1 | 12/2013 | Sipos et al. |
| 2017/0113995 A1 | 4/2017 | Mastrangelo et al. |
| 2019/0390035 A1 | 12/2019 | Essaddam et al. |

FOREIGN PATENT DOCUMENTS

| | | |
|---|---|---|
| CA | 2069500 A1 | 6/1991 |
| CN | 1585798 A | 2/2005 |
| CN | 102746460 A | 10/2012 |
| CN | 104327254 A | 2/2015 |
| CN | 105601507 A | 5/2016 |
| EP | 1710226 A1 | 10/2006 |
| FR | 2335490 A1 | 7/1977 |
| GB | 784248 A | 10/1957 |
| JP | 2001192492 A | 7/2001 |
| JP | 2001261707 A | 9/2001 |
| JP | 2006045371 A | 2/2006 |
| JP | 4365592 B2 | 11/2009 |
| JP | 4575074 B2 | 11/2010 |
| JP | 2014070132 A | 4/2014 |
| WO | WO-9527753 A1 | 10/1995 |

(Continued)

OTHER PUBLICATIONS

ACS. Common Organic Solvents: Table of Properties. downloaded from https://www.organicdivision.org/orig/organic_solvents.html on Apr. 4, 2018, p. 1-2).
Adeakin et al. Polymer-Solvent Relation: Swelling and Fibre Morphology. IOSR-JPTE 4(2):27-28 (2017).
Balcerzyk. Behavior of swollen poly(ethylene terephthalate) on the action of alkali solutions. Kolloid-Z.u.Z. Polymere 251:776-778 (1973).
Co-pending U.S. Appl. No. 15/706,484, filed Sep. 15, 2017.
Falbe. Alcohols, Aliphatic—Ullmann's Encyclopedia of Industrial Chemistry. Downloaded from https://doi.org/10.1002/14356007.a01_279.pub2, first published Jan. 15, 2013, p. 1-26.

(Continued)

*Primary Examiner* — Amy C Bonaparte

(74) *Attorney, Agent, or Firm* — Wilson Sonsini Goodrich & Rosati

(57) ABSTRACT

The present invention relates to the depolymerization of polymers and the recovery of the starting materials used for the production of the polymer. The present invention also relates to the depolymerization of polyethylene terephthalate (PET) and the recovery of terephthalic acid and ethylene glycol.

18 Claims, No Drawings

(56) References Cited

FOREIGN PATENT DOCUMENTS

| WO | WO-9724310 A1 | 7/1997 |
|---|---|---|
| WO | WO-9746611 A1 | 12/1997 |
| WO | WO-9803459 A1 | 1/1998 |
| WO | WO-0047659 A1 | 8/2000 |
| WO | WO-0158982 A1 | 8/2001 |
| WO | WO-0218471 A2 | 3/2002 |
| WO | WO-0238276 A1 | 5/2002 |
| WO | WO-2005003217 A1 | 1/2005 |
| WO | WO-2006021063 A1 | 3/2006 |
| WO | WO-2007076384 A2 | 7/2007 |
| WO | WO-2007096326 A1 | 8/2007 |
| WO | WO-2007113872 A1 | 10/2007 |
| WO | WO-2007148353 A1 | 12/2007 |
| WO | WO-2008007384 A1 | 1/2008 |
| WO | WO-2017007965 A1 | 1/2017 |
| WO | WO-2019051597 A1 | 3/2019 |

OTHER PUBLICATIONS

Feghali et al. Room Temperature Organocatalyzed Reductive Depolymerization of Waste Polyethers Polyesters and Polycarbonates. ChemSusChem. 8(6):980-984 (2015).

Haga. Anomalous Swelling of Poly(ethylene terephthalate) fiber in organic solvents. Journal of Polymer Science, Polymer Letters Edition 20:629-634 (1982).

Haga. Case II swelling of poly(ethylene terephthalate) in organic solvents. Journal of Applied Polymer Science 26(8):2649-2655 (1981).

Kurokawa et al. Methanolysis of polyethylene terephthalate (PET) in the presence of aluminium tiisopropoxide catalyst to form dimethyl terephthalate and ethylene glycol. Polymer Degradation and Stability 79(3):529-533 (2003).

Mishra et al. Kinetic and thermodynamic study of methanolysis of poly(ethylene terephthalate) waste powder. Polym Int 52:337-342 (2003).

Namboori et al. Steric effects in the basic hydrolysis of poly(ethylene terephthalate). Journal of Applied Polymer Science 12:1999-2005 (1968).

PCT/US2016/041392 International Preliminary Report on Patentability dated Jan. 18, 2018.

PCT/US2016/041392 International Search Report and Written Opinion dated Nov. 10, 2016.

Ramsden et al. Factors Influencing the Kinetics of the Alkaline Depolymerisation of Poly(ethylene terephthalate) I: The Effect of Solvent. J Chem Tech Biotechnol 67:131-136 (1996).

Sheehan. Terephthalic Acid, Dimethyl Terephthalate, and Isophthalic Acid. Ullmann's Encyclopedia of Industrial Chemistry 36:17-28 (2011).

U.S. Appl. No. 14/795,116 Office Action dated Jun. 2, 2016.
U.S. Appl. No. 15/377,460 Office Action dated Jan. 29, 2018.
U.S. Appl. No. 15/706,484 Office Action dated Apr. 13, 2018.
U.S. Appl. No. 15/706,484 Office Action dated Oct. 15, 2018.

Venkatachalam et al. Materials Science "Polyester"—Chapter 4: Degradation and Recyclability of Poly(Ehtylene Terephthalate). Intech 24 pgs. (2012).

PCT/CA2018/051135 International Search Report and Written Opinion dated Dec. 4, 2018.

PCT/162019/000816 International Search Report and Written Opinion dated Jan. 3, 2020.

Shukla et al. Glycolysis of polyethylene terephthalate waste fibers. Journal of Applied Polymer Science 98:513-517 (2005).

\* cited by examiner

POLYETHYLENE TEREPHTHALATE DEPOLYMERIZATION

CROSS-REFERENCE TO RELATED APPLICATIONS

This application is a continuation of U.S. patent application Ser. No. 15/377,460, filed on Dec. 13, 2016, now U.S. Pat. No. 10,087,130, issued on Oct. 2, 2018, which is a continuation of U.S. patent application Ser. No. 14/795,116, filed on Jul. 9, 2015, now U.S. Pat. No. 9,550,713, issued on Jan. 24, 2017, all of which are incorporated by reference in their entirety.

FIELD OF THE INVENTION

The present invention relates to the depolymerization of polymers and the recovery of the starting materials used for the production of a new polymer. The present invention also relates to the depolymerization of polyethylene terephthalate (PET) and the recovery of terephthalic acid and ethylene glycol.

BACKGROUND OF THE INVENTION

PET recycling methods are categorized into four groups namely primary, secondary, tertiary, and quaternary recycling.

SUMMARY OF THE INVENTION

In one aspect, is a process for depolymerizing a polymer comprising an ester functionality to starting materials for use in the production of new polymers, comprising admixing the polymer with a mixture of (i) a non-polar solvent capable of swelling the polymer; and (ii) an agent capable of breaking the ester functionality; wherein the admixing is continued for a sufficient time to depolymerize at least a portion of the polymer to the starting materials; and wherein the process is performed without applying external heat.

In some embodiments, the agent capable of breaking the ester functionality is a mixture of an alcohol and a hydroxide.

In some embodiments, the mixture of the alcohol and the hydroxide is added to the polymer simultaneously with the non-polar solvent.

In some embodiments, the ratio of the non-polar solvent to alcohol is about 1:10 to about 1:50 (v:v).

In some embodiments, the polymer is admixed with the non-polar solvent, the hydroxide, and the alcohol for about 0 h to about 5 h.

In some embodiments, the polymer is admixed with the non-polar solvent, the hydroxide, and the alcohol at atmospheric pressure.

In some embodiments, the non-polar solvent capable of swelling the polymer is a halogenated solvent.

In some embodiments, the alcohol is a linear $C_1$-$C_4$ alcohol.

In some embodiments, the hydroxide is selected from a group consisting of an alkali metal hydroxide, an alkaline earth metal hydroxide, an ammonium hydroxide, and a combination thereof.

In some embodiments, the polymer is in the form of waste material.

In some embodiments, the waste material further comprises debris that does not include the polymer comprising the ester functionality.

In some embodiments, the debris comprises at least one of bottle caps, glue, paper, residual liquid, and dirt.

In some embodiments, the polymer comprising the ester functionality is polyethylene terephthalate and the starting materials for the production of the polymer are terephthalic acid or salt thereof and ethylene glycol.

In some embodiments, the terephthalic acid or salt thereof contains less than about 1% impurity (w/w).

In some embodiments, the impurity comprises at least one of isophthalic acid, phthalic acid, 4-methylbenzoic acid, 4-formylbenzoic acid, and metals.

In another aspect, is a process for depolymerizing polymer comprising an ester functionality to starting materials for use in the production of new polymers, comprising admixing the polymer with a mixture of (i) about 3 to about 5% (vol.) of a non-polar solvent capable of swelling the polymer, wherein the non-polar solvent is a halogenated solvent; (ii) about 95 to about 97% (vol.) of a linear $C_1$-$C_4$ alcohol; and (iii) a hydroxide; wherein the admixing is continued for about 1 h; and wherein the process is performed without applying external heat.

In some embodiments, the polymer comprising the ester functionality is polyethylene terephthalate and the starting materials for the production of the polymer are terephthalic acid or salt thereof and ethylene glycol.

In some embodiments, the terephthalic acid or salt thereof contains less than about 1% impurity (w/w).

In some embodiments, the impurity comprises at least one of isophthalic acid, phthalic acid, 4-methylbenzoic acid, 4-formylbenzoic acid, and metals.

In another aspect, is a process for depolymerizing of polyethylene terephthalate to terephthalic acid or salt thereof and ethylene glycol comprising admixing polyethylene terephthalate with a mixture of: (i) about 3 to about 5% (vol.) of a non-polar solvent capable of swelling the polymer, wherein the non-polar solvent is a halogenated solvent; (ii) about 95 to about 97% (vol.) of a linear $C_1$-$C_4$ alcohol; and (iii) a hydroxide; wherein the admixing is continued for about 1 h; and wherein the process is performed without applying external heat.

DETAILED DESCRIPTION OF THE INVENTION

The conversion of many esters to acids and alcohols is carried out by boiling the ester in a mixture of base and alcohol. However, the conversion of some esters is very difficult as is the conversion of polyesters to their corresponding acids and glycols. Polyesters are normally not soluble in the solvents that are used for the conversion of esters to alcohol and acid. Also, polyesters are often highly crystallized, further limiting their solubility and hindering the attack of the ester bonds by a base.

Polyethylene terephthalate (sometimes written poly(ethylene terephthalate)), commonly abbreviated as PET, is the most common thermoplastic polymer resin of the polyester family and is used in fibers for clothing, containers for liquids and foods, thermoforming for manufacturing, and in combination with glass fiber for engineering resins. It is also referred to by the brand name Mylar®, Decron®, Terylene®, or Recron®.

The majority of the world's PET production is for synthetic fibers (in excess of 60%), with bottle production accounting for about 30% of global demand. Polyester makes up about 18% of world polymer production and is the third-most-produced polymer; polyethylene (PE) and polypropylene (PP) are first and second, respectively.

PET consists of polymerized units of the monomer ethylene terephthalate, with repeating $(C_{10}H_8O_4)$ units (Formula I):

Formula I

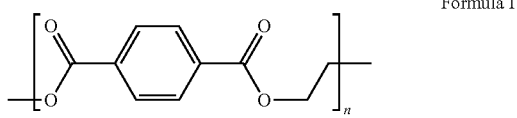

Depending on its processing and thermal history, polyethylene terephthalate exists both as an amorphous (transparent) and as a semi-crystalline polymer. The semicrystalline material might appear transparent (particle size <500 nm) or opaque and white (particle size up to a few micrometers) depending on its crystal structure and particle size. Its monomer bis(2-hydroxyethyl) terephthalate is optionally synthesized by the esterification reaction between terephthalic acid and ethylene glycol with water as a byproduct, or by transesterification reaction between ethylene glycol and dimethyl terephthalate with methanol as a byproduct. Polymerization is through a polycondensation reaction of the monomers (done immediately after esterification/transesterification) with water as the byproduct.

Because PET is an excellent water and moisture barrier material, plastic bottles made from PET are widely used for soft drinks. For certain specialty bottles, such as those designated for beer containment, PET sandwiches an additional polyvinyl alcohol (PVOH) layer to further reduce its oxygen permeability.

Biaxially oriented PET film (often known by one of its trade names, Mylar®) can be aluminized by evaporating a thin film of metal onto it to reduce its permeability, and to make it reflective and opaque (MPET). These properties are useful in many applications, including flexible food packaging and thermal insulation. Because of its high mechanical strength, PET film is often used in tape applications, such as the carrier for magnetic tape or backing for pressure-sensitive adhesive tapes. It is used to make the fabric polar fleece.

Non-oriented PET sheet can be thermoformed to make packaging trays and blister packs. When crystallizable PET is used, the trays can be used for frozen dinners, since they withstand both freezing and oven baking temperatures. As opposed to amorphous PET, which is transparent, crystallizable PET or CPET tends to be black in color.

PET is also used as substrate in thin film and solar cell.

Primary Recycling:

Primary recycling, also known as re-extrusion, is the oldest way of recycling PET. It refers to the "in-plant" recycling of the scrap materials that have similar features to the original products. This process ensures simplicity and low cost, but requires uncontaminated scrap, and only deals with single-type waste, making it an unpopular choice for recyclers.

Secondary Recycling:

Secondary recycling, also known as mechanical recycling, was commercialized in the 1970s. It involves separation of the polymer from its contaminants and reprocessing it to granules via mechanical means. Mechanical recycling steps include sorting and separation of wastes, removal of contaminants, reduction of size by crushing and grinding, extrusion by heat, and reforming. The more complex and contaminated the waste is, the more difficult it is to recycle mechanically. Among the main issues of secondary recycling are the heterogeneity of the solid waste, and the degradation of the product properties each time it is recycled. Since the reactions in polymerization are all reversible in theory, the employment of heat results to photo-oxidation and mechanical stresses, causing deterioration of the product's properties. Another problem is the undesirable gray color resulting from the wastes that have the same type of resin, but of different color.

Tertiary Recycling:

Tertiary recycling, more commonly known as chemical recycling, involves the transformation of the PET polymer chain. Usually by means of solvolytic chain cleavage, this process can either be a total depolymerization back to its monomers or a partial depolymerization to its oligomers and other industrial chemicals. Since PET is a polyester with functional ester groups, it can be cleaved by some reagents such as water, alcohols, acids, glycols, and amines. Also, PET is formed through a reversible polycondensation reaction, so it can be transformed back to its monomer or oligomer units by pushing the reaction to the opposite direction through the addition of a condensation product. These low molecular products can then be purified and reused as raw materials to produce high quality chemical products (Carta et al., 2003, Environmental Science And Pollution Research, Vol. 10, No. 6, pp. 390-394). Among the recycling methods, chemical recycling is the most established and the only one acceptable according to the principles of 'sustainable development', defined as development that meets the needs of present generation without compromising the ability of future generations to meet their needs, because it leads to the formation of the raw materials (monomers) from which the polymer is originally made. In this way the environment is not surcharged and there is no need for extra resources for the production of PET. There are three main methods in PET chemical recycling depending on the added hydroxyl bearing molecule: glycol for glycolysis, methanol for methanolysis, and water for hydrolysis. Other methods include aminolysis and ammonolysis.

Hydrolysis:

Hydrolysis involves the depolymerization of PET to terephthalic acid (TPA) and ethylene glycol by the addition of water in acidic, alkaline or neutral environment. The hydrolysis products is optionally used to produce virgin PET, or is optionally converted to more expensive chemicals like oxalic acid (Yoshioka et al., 2003, Ind. Eng. Chem. Res., Vol. 42, No. 4, pp. 675-679). Concentrated sulfuric acid is usually used for acid hydrolysis (U.S. Pat. Nos. 3,952,053; 4,355,175), caustic soda for alkaline hydrolysis (Alter, 1986, Encyclopedia of Polymer Science and Engineering, pp. 103-128, Herman Mark, Wiley Interscience), and water or steam for neutral hydrolysis (Campanelli et al., J. Appl. Polym. Sci., Vol. 48, No. 3, (April 1993), pp. 443-451 and Campanelli et al., J. Appl. Polym. Sci., Vol. 53, No. 8, (August 1994), pp. 985-991). Hydrolysis is slow compared to methanolysis and glycolysis, because among the three depolymerizing agents (i.e. water, methanol, ethylene glycol), water is the weakest nucleophile. It also always uses high temperatures or high pressures or a combination thereof. Another disadvantage of hydrolysis is the difficulty of recovery of the TPA monomer, which requires numerous steps in order to reach the required purity.

Methanolysis:

Methanolysis is the depolymerization of PET to dimethyl terephthalate (DMT) and ethylene glycol (EG) by methanol.

Glycolysis:

Glycolysis is carried out using ethylene glycol to produce bis(2-hydroxyethyl) terephthalate (BHET) and other PET glycolyzates, which can be used to manufacture unsaturated resins, polyurethane foams, copolyesters, acrylic coatings and hydrophobic dystuffs. The BHET produced through glycolysis can be added with fresh BHET and the mixture can be used in any of the two PET production (DMT-based or TPA-based) lines. Besides its flexibilty, glycolysis is the simplest, oldest, and least capital-intensive process. Because of these reasons, much attention has been devoted to the glycolysis of PET. Numerous works have been published about PET glycolysis, wherein the reaction has been conducted in a wide range of temperature and time.

Studies on the kinetics of PET glycolysis have shown that glycolysis without a catalyst (such as metal salts, zeolites, or ionic liquids) is very slow and complete depolymerization of PET to BHET cannot be achieved. It also yields an end product that contains significant amount of other oligomers in addition to the BHET monomer. This results in difficulty in recovering the BHET monomer when it is the desired product. Thus, research efforts have been directed towards increasing the rate and BHET monomer yield by developing highly efficient catalysts and other techniques, and optimizing the reaction conditions (e.g. temperature, time, PET/EG ratio, PET/catalyst ratio).

Quaternary Recycling:

Quaternary recycling represents the recovery of energy content from the plastic waste by incineration. When the collection, sorting and separation of plastics waste are difficult or economically not viable, or the waste is toxic and hazardous to handle, the best waste management option is incineration to recover the chemical energy stored in plastics waste in the form of thermal energy. However, it is thought to be ecologically unacceptable due to potential health risks from the air born toxic substances.

An Improvement in PET Recycling

Due to the growing use of polyethylene terephthalate in the packaging and fiber (carpet and other textile) industries there is a need for an efficient, low energy, high yielding, and cost effective way to depolymerize polyethylene terephthalate to generate terephthalic acid and ethylene glycol in order to regenerate polyethylene terephthalate.

In some embodiments, the process of the present invention is useful for the depolymerization of polymers comprising an ester functionality in whatever form, such as bulk waste material, since the conversion is rapid and does not require a grinding step. In some embodiments, polymer flakes are used. In some embodiments, the polymers are mixed in with debris, such as, but not limited to, bottle caps, glue, paper, residual liquid, dirt, or a combination thereof.

In some embodiments, the polymer comprising an ester functionality is selected from polyethylene terephthalate (PET), polyglycolide or polyglycolic acid (PGA), polylactic acid (PLA), polycaprolactone (PCL), polyhydroxyalkanoate (PHA), polyhydroxybutyrate (PHB), polyethylene adipate (PEA), polybutylene succinate (PBS), poly(3-hydroxybutyrate-co-3-hydroxyvalerate) (PHBV), polybutylene terephthalate (PBT), polytrimethylene terephthalate (PTT), polyethylene naphthalate (PEN), vectran, and a combination thereof.

In some embodiments, the polymer comprising an ester functionality is polyethylene terephthalate (PET).

In some embodiments, the polymer comprising an ester functionality is a terephthalic acid/ethylene glycol oligomer.

In some embodiments, the polymer comprising an ester functionality is a dicarboxylic acid/dialcohol oligomer, wherein the dicarboxylic acid is selected from the group consisting of naphthalene dicarboxylic acid, diphenyldicarboxylic acid, diphenyl ether dicarboxylic acid, diphenylsulfonedicarboxylic acid, diphenoxyethanedicarboxylic acid, succinic acid, adipic acid, sebacic acid, azelaic acid, decanedicarboxylic acid, cyclohexanedicarboxylic acid, trimellitic acid, pyromellitic acid, and a combination thereof, and the dialcohol is selected from the group consisting of trimethylene glycol, 1,2-propanediol, tetramethylene glycol, neopentyl glycol, hexamethylene glycol, decanemethylene glycol, dodecamethylene glycol, 1,4-cyclohexanedimethanol, diethylene glycol, triethylene glycol, tetraethylene glycol, polyethylene glycol, dipropylene glycol, tripropylene glycol, tetrapropylene glycol, polypropylene glycol, di(tetramethylene) glycol, tri(tetramethylene) glycol, polytetramethylene glycol, pentaerythritol, 2,2-bis(4-β-hydroxyethoxyphenyl)propane, and a combination thereof.

In some embodiments, the process of the present invention is useful for the depolymerization of polyethylene terephthalate in whatever form, such as bulk waste material, since the conversion is rapid and does not require a grinding step. In some embodiments, the waste material is washed prior to the depolymerization. In some embodiments, the waste material is not washed prior to the depolymerization. In some embodiments, polymer flakes are used. In some embodiments, polyethylene terephthalate is mixed in with debris, such as, but not limited to, bottle caps, glue, paper, residual liquid, dirt, or a combination thereof.

In some embodiments, the process of the present invention is useful for the selective depolymerization of polymers comprising an ester functionality wherein the polymer comprising an ester functionality is mixed with other polymers such as, for example, but not limited to, polyethylene, high density polyethylene, low density polyethylene, polypropylene, or a combination thereof.

In some embodiments, the process of the present invention is useful for the selective depolymerization of polyethylene terephthalate wherein polyethylene terephthalate is mixed with other polymers such as, for example, but not limited to, polyethylene, high density polyethylene, low density polyethylene, polypropylene, or a combination thereof.

In some embodiments, the process of the present invention is useful for depolymerizing a polymer comprising an ester functionality to starting materials for use in the production of new polymers, comprising admixing the polymer with a mixture of (i) a non-polar solvent capable of swelling the polymer; and (ii) an agent capable of breaking the ester functionality; wherein the admixing is continued for a sufficient time to depolymerize at least a portion of the polymer to the starting materials; and wherein the process is performed without applying external heat.

In some embodiments, the non-polar solvent is a solvent capable of breaking hydrogen bonds in the polymers. In some embodiments, the non-polar solvent is capable of swelling the polymers. In some embodiments, the non-polar solvent is capable of dissolving the polymers. In some embodiments, the non-polar solvent is an aprotic non-polar solvent. In some embodiments, the non-polar solvent is a halogenated solvent. In some embodiments, the non-polar solvent is a chlorinated solvent. In some embodiments, the non-polar solvent is dichloromethane, dichloroethane, tetrachloroethane, chloroform, tetrachloromethane, trichloroethane, or a combinations thereof.

In some embodiments, the agent capable of breaking the ester functionality is a mixture of an alcohol and a base. In some embodiments, the agent capable of breaking the ester functionality is a mixture of an alcohol and an acid.

In some embodiments, the alcohol used in the agent capable of breaking the ester functionality is an alcohol that is capable of dissolving the base. In some embodiments the alcohol is a linear, branched, cyclic alcohol, or a combination thereof. In some embodiments, the alcohol is a linear $C_1$-$C_4$ alcohol. In some embodiments, the alcohol is methanol, ethanol, propanol, butanol, or a combination thereof. In some embodiments, the alcohol is methanol, ethanol, propanol, or a combination thereof. In some embodiments, the alcohol is methanol. In some embodiments, the alcohol is ethanol. In some embodiments, the alcohol is a branched $C_3$-$C_4$ alcohol. In some embodiments, the alcohol is t-butanol, s-butanol, i-butanol, i-propanol, s-propanol, or a combination thereof. In some embodiments, the alcohol is a cyclic $C_3$-$C_8$ alcohol. In some embodiments, the alcohol is cyclopropanol, cyclobutanol, cyclopentanol, cyclohexanol, cycloheptanol, or a combination thereof.

In some embodiments, the base used in the agent capable of breaking the ester functionality is a base that is substantially soluble in the final solution.

In some embodiments, the base capable of breaking the ester functionality is an alkoxide. In some embodiments, the alkoxide is a $C_1$-$C_4$ alkoxide. In some embodiments, the alkoxide is selected from a group consisting of methoxide, ethoxide, n-propoxide, n-butoxide, t-butoxide, s-butoxide, i-butoxide, i-propoxide, s-propoxide, and a combination thereof. In some embodiments, the alkoxide is methoxide, ethoxide, or a combination thereof.

In some embodiments, the base capable of breaking the ester functionality is a hydroxide. In some embodiments, the hydroxide is selected from the group consisting of alkali metal hydroxide, alkaline-earth metal hydroxide, and ammonium hydroxide, and a combination thereof. In some embodiments, the hydroxide is selected from a group consisting of sodium hydroxide, potassium hydroxide, calcium hydroxide, lithium hydroxide, magnesium hydroxide, ammonium hydroxide, tetra-alkyl ammonium hydroxide, and a combination thereof. In some embodiments, the hydroxide is sodium hydroxide, potassium hydroxide, or a combination thereof. In some embodiments, the hydroxide is sodium hydroxide. In some embodiments, the hydroxide is potassium hydroxide. In some embodiments, the hydroxide is a mixture of sodium hydroxide and potassium hydroxide.

In some embodiments, the acid used in the agent capable of breaking the ester functionality is an organic acid. In some embodiments, the acid used in the agent capable of breaking the ester functionality is an inorganic acid. In some embodiments, the acid is sulfuric acid, hydrochloric acid, or a combination thereof.

In some embodiments, the molar ratio of base or acid to the ester bonds present in the polymer is greater than 1:1. In some embodiments, the molar ratio of base to the ester bonds present in the polymer is greater than 1:1. In some embodiments, the molar ratio of hydroxide to the ester bonds present in the polymer is greater than 1:1. In some embodiments, the molar ratio of alkoxide to the ester bonds present in the polymer is greater than 1:1. In some embodiments, the molar ratio of base or acid to the ester bonds present in the polymer is lower than 1:1. In some embodiments, the molar ratio of base to the ester bonds present in the polymer is lower than 1:1. In some embodiments, the molar ratio of hydroxide to the ester bonds present in the polymer is lower than 1:1. In some embodiments, the molar ratio of alkoxide to the ester bonds present in the polymer is lower than 1:1. In some embodiments, the molar ratio of base or acid to the ester bonds present in the polymer is about 1:1. In some embodiments, the molar ratio of base to the ester bonds present in the polymer is about 1:1. In some embodiments, the molar ratio of hydroxide to the ester bonds present in the polymer is about 1:1. In some embodiments, the molar ratio of alkoxide to the ester bonds present in the polymer is about 1:1.

In some embodiments, the mixture of the alcohol and the base or acid is added to the polymer prior to the addition of the non-polar solvent. In some embodiments, the mixture of the alcohol and the base or acid is added to the polymer after the addition of the non-polar solvent. In some embodiments, the mixture of the alcohol and the base or acid is added to the polymer simultaneously with the non-polar solvent. In some embodiments, the mixture of the alcohol and the base is added to the polymer simultaneously with the non-polar solvent. In some embodiments, the mixture of the alcohol and the hydroxide is added to the polymer simultaneously with the non-polar solvent. In some embodiments, the mixture of the alcohol and the alkoxide is added to the polymer simultaneously with the non-polar solvent. In some embodiments the base is dissolved in the alcohol prior to the addition to the non-polar solvent.

In some embodiments, the ratio of the non-polar solvent to alcohol is from about 1:1 (v:v) to about 1:100 (v:v). In some embodiments, the ratio of the non-polar solvent to alcohol is from about 1:1 (v:v) to about 1:10 (v:v). In some embodiments, the ratio of the non-polar solvent to alcohol is from about 1:10 (v:v) to about 1:20 (v:v). In some embodiments, the ratio of the non-polar solvent to alcohol is from about 1:20 (v:v) to about 1:30 (v:v). In some embodiments, the ratio of the non-polar solvent to alcohol is from about 1:30 (v:v) to about 1:40 (v:v). In some embodiments, the ratio of the non-polar solvent to alcohol is from about 1:40 (v:v) to about 1:50 (v:v). In some embodiments, the ratio of the non-polar solvent to alcohol is from about 1:50 (v:v) to about 1:60 (v:v). In some embodiments, the ratio of the non-polar solvent to alcohol is from about 1:60 (v:v) to about 1:70 (v:v). In some embodiments, the ratio of the non-polar solvent to alcohol is from about 1:70 (v:v) to about 1:80 (v:v). In some embodiments, the ratio of the non-polar solvent to alcohol is from about 1:80 (v:v) to about 1:90 (v:v). In some embodiments, the ratio of the non-polar solvent to alcohol is from about 1:90 (v:v) to about 1:100 (v:v). In some embodiments, the ratio of the non-polar solvent to alcohol is from about 1:1 (v:v) to about 1:50 (v:v). In some embodiments, the ratio of the non-polar solvent to alcohol is from about 1:2 (v:v) to about 1:50 (v:v). In some embodiments, the ratio of the non-polar solvent to alcohol is from about 1:3 (v:v) to about 1:50 (v:v). In some embodiments, the ratio of the non-polar solvent to alcohol is from about 1:4 (v:v) to about 1:50 (v:v). In some embodiments, the ratio of the non-polar solvent to alcohol is from about 1:5 (v:v) to about 1:50 (v:v). In some embodiments, the ratio of the non-polar solvent to alcohol is from about 1:6 (v:v) to about 1:50 (v:v). In some embodiments, the ratio of the non-polar solvent to alcohol is from about 1:7 (v:v) to about 1:50 (v:v). In some embodiments, the ratio of the non-polar solvent to alcohol is from about 1:8 (v:v) to about 1:50 (v:v). In some embodiments, the ratio of the non-polar solvent to alcohol is from about 1:9 (v:v) to about 1:50 (v:v). In some embodiments, the ratio of the non-polar solvent to alcohol is from about 1:10 (v:v) to about 1:50 (v:v). In some embodiments, the ratio of the non-polar solvent to alcohol is about 1:10 (v:v), about 1:11 (v:v), about 1:12 (v:v), about 1:13 (v:v), about 1:14 (v:v), about 1:15 (v:v), about 1:16 (v:v), about 1:17 (v:v), about 1:18 (v:v), about 1:19 (v:v), about 1:20 (v:v), about 1:21 (v:v), about 1:22 (v:v), about 1:23 (v:v), about 1:24 (v:v), about 1:25 (v:v), about 1:26 (v:v), about 1:27 (v:v), about 1:28 (v:v), about 1:29 (v:v), about 1:30 (v:v), about 1:31 (v:v), about 1:32 (v:v), about 1:33 (v:v), about 1:34 (v:v), about 1:35 (v:v), about 1:36 (v:v), about 1:37 (v:v), about 1:38 (v:v), about 1:39 (v:v), about 1:40 (v:v), about 1:41 (v:v), about 1:42 (v:v), about 1:43 (v:v), about 1:44 (v:v), about 1:45 (v:v), about 1:46 (v:v), about 1:47 (v:v), about 1:48 (v:v), about 1:49 (v:v), or about 1:50 (v:v).

In some embodiments, the amount of alcohol is from about 70% to about 99% (vol.) of the total mixture volume. In some embodiments, the amount of alcohol is from about 95% to about 97% (vol.) of the total mixture volume. In some embodiments, the amount of alcohol is about 70% (vol.), about 71% (vol.), about 72% (vol.), about 73% (vol.), about 74% (vol.), about 75% (vol.), about 76% (vol.), about 77% (vol.), about 78% (vol.), about 79% (vol.), about 80% (vol.), about 81% (vol.), about 82% (vol.), about 83% (vol.), about 84% (vol.), about 85% (vol.), about 86% (vol.), about 87% (vol.), about 88% (vol.), about 89% (vol.), about 90% (vol.), about 91% (vol.), about 92% (vol.), about 93% (vol.), about 94% (vol.), about 95% (vol.), about 96% (vol.), about 97% (vol.), about 98% (vol.), or about 99% (vol.) of the total mixture volume.

In some embodiments, the amount of non-polar solvent is from about 1% to about 30% (vol.) of the total mixture volume. In some embodiments, the amount of non-polar is from about 3% to about 5% (vol.) of the total mixture volume. In some embodiments, the amount of non-polar is about 1% (vol.), about 2% (vol.), about 3% (vol.), about 4% (vol.), about 5% (vol.), about 6% (vol.), about 7% (vol.), about 8% (vol.), about 9% (vol.), about 10% (vol.), 11% (vol.), about 12% (vol.), about 13% (vol.), about 14% (vol.), about 15% (vol.), about 16% (vol.), about 17% (vol.), about 18% (vol.), about 19% (vol.), about 20% (vol.), 21% (vol.), about 22% (vol.), about 23% (vol.), about 24% (vol.), about 25% (vol.), about 26% (vol.), about 27% (vol.), about 28% (vol.), about 29% (vol.), or about 30% (vol.) of the total mixture volume.

In some embodiments, the polymer is admixed with the non-polar solvent and the agent capable of breaking the ester functionality for a sufficient time to depolymerize at least a portion of the polymer to the starting materials for the production of the polymer.

In some embodiments, the depolymerization is instantaneous. In some embodiments, the sufficient time to depolymerize at least a portion of the polymer to the starting materials for the production of new polymer is about 0 h to about 24 h. In some embodiments, the sufficient time to depolymerize at least a portion of the polymer to the starting materials for use in the production of new polymers is about 0 h to about 20 h, about 0 h to about 15 h, about 0 h to about 10 h, 0 h to about 5 h, about 0 h to about 4 h, about 0 h to about 3 h, about 0 h to about 2 h, or about 0 h to about 1 h. In some embodiments, the sufficient time to depolymerize at least a portion of the polymer to the starting materials for the production of the polymer is about 0 h, 0.1 h, 0.2 h, 0.3 h, about 0.4 h, about 0.5 h, about 0.6 h, about 0.7 h, about 0.8 h, about 0.9 h, or about 1 h.

In some embodiments, the process of the present invention is conducted at ambient temperature. In some embodiments, ambient temperature is 25±5° C.

In some embodiments, the process of the present invention is conducted without applying external heat. In some embodiments, the reaction is exothermic and the temperature of the reaction mixture rises to at least 30° C., at least 35° C., at least 40° C., at least 45° C., at least 50° C., at least 55° C., or even at least 60° C. In some embodiments, no external heat sources are used to increase the temperature of the reaction mixture.

In some embodiments, the process of the present invention is conducted with external heat. In some embodiments, the process of the present invention is conducted with external heat at between about 20° C. and about 100° C. In some embodiments, the process of the present invention is conducted at about 20° C., about 21° C., about 22° C., about 23° C., about 24° C., about 25° C., about 26° C., about 27° C., about 28° C., about 29° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C.

In some embodiments, the process of the present invention is conducted at atmospheric pressure. In some embodiments, the process of the present invention is conducted at elevated pressures. In some embodiments, the process of the present invention is conducted at a pressure between about atmospheric and about 220 psi. In some embodiments, the process of the present invention is conducted at about 14 psi, about 15 psi, about 16 psi, about 17 psi, about 18 psi, about 19 psi, about 20 psi, about 30 psi, about 40 psi, about 50 psi, about 60 psi, about 70 psi, about 80 psi, about 90 psi, about 100 psi, about 110 psi, about 120 psi, about 130 psi, about 140 psi, about 150 psi, about 160 psi, about 170 psi, about 180 psi, about 190 psi, about 200 psi, about 210 psi, or about 220 psi.

In some embodiments, the process of the present invention is conducted without agitation. In some embodiments, the process of the present invention is conducted with increased agitation. In some embodiments, a stirred batch reactor is used to provide agitation. In some embodiments, a continuous reactor is used to provide agitation.

In some embodiments, the process of the present invention is conducted without the addition of a catalyst. In some embodiments, the process of the present invention is conducted with the addition of a catalyst. In some embodiments, the catalyst used in the depolymerization process of the present invention comprises at least one of germanium compounds, titanium compounds, antimony compounds, zinc compounds, cadmium compounds, manganese compounds, magnesium compounds, cobalt compounds, silicon compounds, tin compounds, lead compounds, and aluminum compounds.

In some embodiments, the catalyst used in the depolymerization process of the present invention comprises at least one of germanium dioxide, cobalt acetate, titanium tetrachloride, titanium phosphate, titanium tetrabutoxide, titanium tetraisopropoxide, titanium tetra-n-propoxide, titanium tetraethoxide, titanium tetramethoxide, a tetrakis (acetylacetonato)titanium complex, a tetrakis(2,4-hexanedionato)titanium complex, a tetrakis(3,5-heptanedionato)titanium complex, a dimethoxybis(acetylacetonato)titanium complex, a diethoxybis(acetylacetonato)titanium complex, a diisopropoxybis(acetylacetonato)titanium complex, a di-n-propoxybis(acetylacetonato)titanium complex, a dibutoxybis(acetylacetonato)titanium complex, titanium dihydroxybisglycolate, titanium dihydroxybisglycolate, titanium dihydroxybislactate, titanium dihydroxybis(2-hydroxypropionate), titanium lactate, titanium octanediolate, titanium dimethoxybistriethanol aminate, titanium diethoxybistriethanol aminate, titanium dibutoxybistriethanol aminate, hexamethyl dititanate, hexaethyl dititanate, hexapropyl dititanate, hexabutyl dititanate, hexaphenyl dititanate, octamethyl trititanate, octaethyl trititanate, octapropyl trititanate, octabutyl trititanate, octaphenyl trititanate, a hexaalkoxy dititanate, zinc acetate, manganese acetate, methyl silicate, zinc chloride, lead acetate, sodium carbonate, sodium bicarbonate, acetic acid, sodium sulfate, potassium sulfate, zeolites, lithium chloride, magnesium chloride, ferric chloride, zinc oxide, magnesium oxide, calcium oxide, barium oxide, antimony trioxide, and antimony triacetate.

In some embodiments, the process of the present invention is useful for depolymerizing a polymer comprising and ester functionality to starting materials for use in the production of new polymers comprising admixing the polymer with a mixture of (i) about 3 to about 5% (vol.) of a non-polar solvent capable of swelling the polymer, wherein the non-polar solvent is a chlorinated solvent; (ii) about 95 to about 97% (vol.) of a linear $C_1$-$C_4$ alcohol; and (iii) a hydroxide; wherein the admixing is continued for about 1 h; and wherein the process is performed without applying external heat.

In some embodiments, the polymer comprising and ester functionality is polyethylene terephthalate. In some embodiments, the starting materials for use in the production of new polymers is selected from the group consisting of terephthalic acid/ethylene glycol oligomers or salt thereof, terephthalic acid or salt thereof, 4-(methoxycarbonyl)benzoic acid or a salt thereof, ethylene glycol, and a combination thereof.

In some embodiments, the starting materials for use in the production of new polymers are terephthalic acid or salt thereof and ethylene glycol.

In some embodiments, the starting materials for use in the production of new polymers are 4-(methoxycarbonyl)benzoic acid or salt thereof and ethylene glycol.

In some embodiments, the starting materials for use in the production of new polymers are terephthalic acid/ethylene glycol oligomers.

In some embodiments, the process of the present invention is useful for depolymerizing polyethylene terephthalate to terephthalic acid or salt thereof and ethylene glycol comprising admixing polyethylene terephthalate with a mixture of (i) a non-polar solvent capable of swelling the polymer; and (ii) an agent capable of breaking the ester functionality; wherein the admixing is continued for a sufficient time to depolymerize at least a portion of polyethylene terephthalate to terephthalic acid or salt thereof and ethylene glycol; and wherein the process is performed without applying external heat.

In some embodiments, the process of the present invention is useful for depolymerizing polyethylene terephthalate to 4-(methoxycarbonyl)benzoic acid or salt thereof and ethylene glycol comprising admixing polyethylene terephthalate with a mixture of (i) a non-polar solvent capable of swelling the polymer; and (ii) an agent capable of breaking the ester functionality; wherein the admixing is continued for a sufficient time to depolymerize at least a portion of polyethylene terephthalate to 4-(methoxycarbonyl)benzoic acid or salt thereof and ethylene glycol; and wherein the process is performed without applying external heat.

In some embodiments, the process of the present invention is useful for depolymerizing polyethylene terephthalate to terephthalic acid or salt thereof and ethylene glycol comprising admixing polyethylene terephthalate with a mixture of (i) about 3 to about 5% (vol.) of a non-polar solvent capable of swelling polyethylene terephthalate, wherein the non-polar solvent is a chlorinated solvent; (ii) about 95 to about 97% (vol.) of a linear $C_1$-$C_4$ alcohol; and (iii) a hydroxide; wherein the admixing is continued for about 1 h; and wherein the process is performed without applying external heat.

In some embodiments, the process of the present invention is useful for depolymerizing polyethylene terephthalate to 4-(methoxycarbonyl)benzoic acid or salt thereof and ethylene glycol comprising admixing polyethylene terephthalate with a mixture of (i) about 3 to about 5% (vol.) of a non-polar solvent capable of swelling polyethylene terephthalate, wherein the non-polar solvent is a chlorinated solvent; (ii) about 95 to about 97% (vol.) of a linear $C_1$-$C_4$ alcohol; and (iii) a hydroxide; wherein the admixing is continued for about 1 h; and wherein the process is performed without applying external heat.

In some embodiments, the starting materials for use in the production of new polymers obtained from depolymerizing a polymer comprising and ester functionality contain less than about 10% impurity (w/w). In some embodiments, the starting materials for use in the production of new polymers obtained from depolymerizing a polymer comprising and ester functionality contain less than about 9% impurity (w/w). In some embodiments, the starting materials for use in the production of new polymers obtained from depolymerizing a polymer comprising and ester functionality contain less than about 8% impurity (w/w). In some embodiments, the starting materials for use in the production of new polymers obtained from depolymerizing a polymer comprising and ester functionality contain less than about 7% impurity (w/w). In some embodiments, the starting materials for use in the production of new polymers obtained from depolymerizing a polymer comprising and ester functionality contain less than about 6% impurity (w/w). In some embodiments, the starting materials for use in the production of new polymers obtained from depolymerizing a polymer comprising and ester functionality contain less than about 5% impurity (w/w). In some embodiments, the starting materials for use in the production of new polymers obtained from depolymerizing a polymer comprising and ester functionality contain less than about 4% impurity (w/w). In some embodiments, the starting materials for use in the production of new polymers obtained from depolymerizing a polymer comprising and ester functionality contain less than about 3% impurity (w/w). In some embodiments, the starting materials for use in the production of new polymers obtained from depolymerizing a polymer comprising and ester functionality contain less than about 2% impurity (w/w). In some embodiments, the starting materials for use in the production of new polymers obtained from depolymerizing a polymer comprising and ester functionality contain less than about 1% impurity (w/w). In some embodiments, the starting materials for use in the production of new polymers obtained from depolymerizing a polymer comprising and ester functionality contain less than about 0.5% impurity (w/w). In some embodiments, the starting materials for use in the production of new polymers obtained from depolymerizing a polymer comprising and ester functionality contain less than about 0.4% impurity (w/w). In some embodiments, the starting materials for use in the production of new polymers obtained from depolymerizing a polymer comprising and ester functionality contain less than about 0.3% impurity (w/w). In some embodiments, the starting materials for use in the production of new polymers obtained from depolymerizing a polymer comprising and ester functionality contain less than about 0.2% impurity (w/w). In some embodiments, the starting materials for use in the production of new polymers obtained from depolymerizing a polymer comprising and ester functionality contain less than about 0.1% impurity (w/w).

In some embodiments, terephthalic acid or salt thereof contains less than about 10% impurity (w/w). In some embodiments, terephthalic acid or salt thereof contains less than about 9% impurity (w/w). In some embodiments, terephthalic acid or salt thereof contains less than about 8% impurity (w/w). In some embodiments, terephthalic acid or salt thereof contains less than about 7% impurity (w/w). In some embodiments, terephthalic acid or salt thereof contains less than about 6% impurity (w/w). In some embodiments, terephthalic acid or salt thereof contains less than about 5% impurity (w/w). In some embodiments, terephthalic acid or salt thereof contains less than about 4% impurity (w/w). In some embodiments, terephthalic acid or salt thereof contains less than about 3% impurity (w/w). In some embodiments, terephthalic acid or salt thereof contains less than about 2% impurity (w/w). In some embodiments, terephthalic acid or salt thereof contains less than about 1% impurity (w/w). In some embodiments, terephthalic acid or salt thereof contains less than about 0.5% impurity (w/w). In some embodiments, terephthalic acid or salt thereof contains less than about 0.4% impurity (w/w). In some embodiments, terephthalic acid or salt thereof contains less than about 0.3% impurity (w/w). In some embodiments, terephthalic acid or salt thereof contains less than about 0.2% impurity (w/w). In some embodiments, terephthalic acid or salt thereof contains less than about 0.1% impurity (w/w).

In some embodiments, 4-(methoxycarbonyl)benzoic acid or salt thereof contains less than about 10% impurity (w/w). In some embodiments, 4-(methoxycarbonyl)benzoic acid or salt thereof contains less than about 9% impurity (w/w). In some embodiments, 4-(methoxycarbonyl)benzoic acid or salt thereof contains less than about 8% impurity (w/w). In some embodiments, 4-(methoxycarbonyl)benzoic acid or salt thereof contains less than about 7% impurity (w/w). In some embodiments, 4-(methoxycarbonyl)benzoic acid or salt thereof contains less than about 6% impurity (w/w). In some embodiments, 4-(methoxycarbonyl)benzoic acid or salt thereof contains less than about 5% impurity (w/w). In some embodiments, 4-(methoxycarbonyl)benzoic acid or salt thereof contains less than about 4% impurity (w/w). In some embodiments, 4-(methoxycarbonyl)benzoic acid or salt thereof contains less than about 3% impurity (w/w). In some embodiments, 4-(methoxycarbonyl)benzoic acid or salt thereof contains less than about 2% impurity (w/w). In some embodiments, 4-(methoxycarbonyl)benzoic acid or salt thereof contains less than about 1% impurity (w/w). In some embodiments, 4-(methoxycarbonyl)benzoic acid or salt thereof contains less than about 0.5% impurity (w/w). In some embodiments, 4-(methoxycarbonyl)benzoic acid or salt thereof contains less than about 0.4% impurity (w/w). In some embodiments, 4-(methoxycarbonyl)benzoic acid or salt thereof contains less than about 0.3% impurity (w/w). In some embodiments, 4-(methoxycarbonyl)benzoic acid or salt thereof contains less than about 0.2% impurity (w/w). In some embodiments, 4-(methoxycarbonyl)benzoic acid or salt thereof contains less than about 0.1% impurity (w/w).

In some embodiments, ethylene glycol obtained contains less than about 10% impurity (w/w). In some embodiments, ethylene glycol contains less than about 9% impurity (w/w). In some embodiments, ethylene glycol contains less than about 8% impurity (w/w). In some embodiments, ethylene glycol contains less than about 7% impurity (w/w). In some embodiments, ethylene glycol contains less than about 6% impurity (w/w). In some embodiments, ethylene glycol contains less than about 5% impurity (w/w). In some embodiments, ethylene glycol contains less than about 4% impurity (w/w). In some embodiments, ethylene glycol contains less than about 3% impurity (w/w). In some embodiments, ethylene glycol contains less than about 2% impurity (w/w). In some embodiments, ethylene glycol contains less than about 1% impurity (w/w). In some embodiments, ethylene glycol contains less than about 0.5% impurity (w/w). In some embodiments, ethylene glycol contains less than about 0.4% impurity (w/w). In some embodiments, ethylene glycol contains less than about 0.3% impurity (w/w). In some embodiments, ethylene glycol contains less than about 0.2% impurity (w/w). In some embodiments, ethylene glycol contains less than about 0.1% impurity (w/w).

In some embodiments, the impurity contained in the starting materials for use in the production of new polymers obtained from depolymerizing polyethylene terephthalate comprises at least one of isophthalic acid, phthalic acid, 4-methylbenzoic acid, and 4-formylbenzoic acid.

In some embodiments, the starting materials for use in the production of new polymers obtained from depolymerizing polyethylene terephthalate contains less than about 100 ppm of 4-formylbenzoic acid, less than about 90 ppm of 4-formylbenzoic acid, less than about 80 ppm of 4-formylbenzoic acid, less than about 70 ppm of 4-formylbenzoic acid, less than about 60 ppm of 4-formylbenzoic acid, less than about 50 ppm of 4-formylbenzoic acid, less than about 40 ppm of 4-formylbenzoic acid, less than about 30 ppm of 4-formylbenzoic acid, less than about 20 ppm of 4-formylbenzoic acid, or less than about 10 ppm of 4-formylbenzoic acid.

In some embodiments, the starting materials for use in the production of new polymers obtained from depolymerizing polyethylene terephthalate contains less than about 200 ppm of 4-methylbenzoic acid, less than about 190 ppm of 4-methylbenzoic acid, less than about 180 ppm of 4-methylbenzoic acid, less than about 170 ppm of 4-methylbenzoic acid, less than about 160 ppm of 4-methylbenzoic acid, less than about 150 ppm of 4-methylbenzoic acid, less than about 140 ppm of 4-methylbenzoic acid, less than about 130 ppm of 4-methylbenzoic acid, less than about 120 ppm of 4-methylbenzoic acid, less than about 110 ppm of 4-methylbenzoic acid, less than about 100 ppm of 4-methylbenzoic acid, less than about 90 ppm of 4-methylbenzoic acid, less than about 80 ppm of 4-methylbenzoic acid, less than about 70 ppm of 4-methylbenzoic acid, less than about 60 ppm of 4-methylbenzoic acid, less than about 50 ppm of 4-methylbenzoic acid, less than about 40 ppm of 4-methylbenzoic acid, less than about 30 ppm of 4-methylbenzoic acid, less than about 20 ppm of 4-methylbenzoic acid, or less than about 10 ppm of 4-methylbenzoic acid.

In some embodiments, the impurity contained in the starting materials for use in the production of new polymers obtained from depolymerizing polyethylene terephthalate comprises metals. In some embodiments, the metal impurity comprises at least one of aluminum, arsenic, calcium, cobalt, chromium, iron, potassium, manganese, molybdenum, sodium, nickel, titanium, and lead.

In some embodiments, the starting materials for use in the production of new polymers obtained from depolymerizing polyethylene terephthalate contains less than about 250 ppm of any metals, less than about 240 ppm of any metals, less than about 230 ppm of any metals, less than about 220 ppm of any metals, less than about 210 ppm of any metals, less than about 200 ppm of any metals, less than about 190 ppm of any metals, less than about 180 ppm of any metals, less than about 170 ppm of any metals, less than about 160 ppm of any metals, less than about 150 ppm of any metals, less than about 140 ppm of any metals, less than about 130 ppm of any metals, less than about 120 ppm of any metals, less than about 110 ppm of any metals, less than about 100 ppm of any metals, less than about 90 ppm of any metals, less than about 80 ppm of any metals, less than about 70 ppm of any metals, less than about 60 ppm of any metals, less than about 50 ppm of any metals, less than about 40 ppm of any metals, less than about 30 ppm of any metals, less than about 20 ppm of any metals, less than about 10 ppm of any metals, less than about 5 ppm of any metals, less than about 4 ppm of any metals, less than about 3 ppm of any metals, less than about 2 ppm of any metals, less than about 1 ppm of any metals, less than about 0.9 ppm of any metals, less than about 0.8 ppm of any metals, less than about 0.7 ppm of any metals, less than about 0.6 ppm of any metals, less than about 0.5 ppm of any metals, less than about 0.4 ppm of any metals, less than about 0.3 ppm of any metals, less than about 0.2 ppm of any metals, less than about 0.1 ppm of any metals, less than about 0.09 ppm of any metals, less than about 0.08 ppm of any metals, less than about 0.07 ppm of any metals, less than about 0.06 ppm of any metals, less than about 0.05 ppm of any metals, less than about 0.04 ppm of any metals, less than about 0.03 ppm of any metals, less than about 0.02 ppm of any metals, or less than about 0.01 ppm of any metals.

In some embodiments, the starting materials for use in the production of new polymers obtained from depolymerizing polyethylene terephthalate contains trace amount of catalysts, inhibitors, or stabilizers. In some embodiments, the catalysts, inhibitors, or stabilizers were present in the starting polyethylene terephthalate. Inhibitors work by interfering with the chain initiation and/or chain propagation steps of the polymerization during manufacture and purification when the monomers are at elevated temperatures. Stabilizers are used in the polymerization process to sequester the catalysts in an attempt to reduce the degradation and discoloration of the polymer comprising an ester functionality. The polymerization catalysts would eventually begin to catalyze or encourage the degradation of the polymer formed in the condensation reaction. For example, degradation of polyethylene terephthalate results in the formation of acetaldehyde and the discoloration or yellowing of polyethylene terephthalate.

In some embodiments, the catalyst comprises at least one of germanium compounds, titanium compounds, antimony compounds, zinc compounds, cadmium compounds, manganese compounds, magnesium compounds, cobalt compounds, silicon compounds, tin compounds, lead compounds, and aluminum compounds.

In some embodiments, the catalyst comprises at least one of germanium dioxide, cobalt acetate, titanium tetrachloride, titanium phosphate, titanium tetrabutoxide, titanium tetraisopropoxide, titanium tetra-n-propoxide, titanium tetraethoxide, titanium tetramethoxide, a tetrakis(acetylacetonato)titanium complex, a tetrakis(2,4-hexanedionato)titanium complex, a tetrakis(3,5-heptanedionato)titanium complex, a dimethoxybis(acetylacetonato)titanium complex, a diethoxybis(acetylacetonato)titanium complex, a diisopropoxybis(acetylacetonato)titanium complex, a di-n-propoxybis(acetylacetonato)titanium complex, a dibutoxybis(acetylacetonato)titanium complex, titanium dihydroxybisglycolate, titanium dihydroxybisglycolate, titanium dihydroxybislactate, titanium dihydroxybis(2-hydroxypropionate), titanium lactate, titanium octanediolate, titanium dimethoxybistriethanol aminate, titanium diethoxybistriethanol aminate, titanium dibutoxybistriethanol aminate, hexamethyl dititanate, hexaethyl dititanate, hexapropyl dititanate, hexabutyl dititanate, hexaphenyl dititanate, octamethyl trititanate, octaethyl trititanate, octapropyl trititanate, octabutyl trititanate, octaphenyl trititanate, a hexaalkoxy dititanate, zinc acetate, manganese acetate, methyl silicate, zinc chloride, lead acetate, sodium carbonate, sodium bicarbonate, acetic acid, sodium sulfate, potassium sulfate, zeolites, lithium chloride, magnesium chloride, ferric chloride, zinc oxide, magnesium oxide, calcium oxide, barium oxide, antimony trioxide, and antimony triacetate.

In some embodiments, the inhibitor comprises at least one of nitrobenzene, butylated hydroxyl toluene (BHT), butylated hydroxyanisole (BHA), diphenyl picryl hydrazyl (DPPH), tertiary-butyl catechol (TBC), hydroquinone, or a combination thereof.

In some embodiments, the stabilizer present in the starting polymer comprising an ester functionality comprises a phosphate, a phosphonate, and a phosphite compound. In some embodiments, the stabilizer present in the starting polymer comprising an ester functionality comprises at least one of polyphosphoric acid, phosphoric acid, organophosphorus compounds, organophosphates, organophosphites, organophosphonates, orthophosphoric acid, metaphosphoric acid, pyrophosphoric acid, tripolyphosphoric acid, phosphorous acid, hypophosphorous acid, bismuth phosphate, monoammonium phosphate, diammonium phosphate, monammonium phosphorite; salts of phosphoric acid esters having at least one free alcoholic hydroxyl group, sodium betaglycerophosphate, calcium betaglycerophosphate, phosphotungstic acid, ammonium phosphotungstate, sodium phosphotungstate, tertiary phosphines, tripropylphosphine, triphenylphosphine, ethylphenyltolylphosphine, quaternary phosphonium compounds, triphenylmethylphosphonium iodide, triphenylbenzylphosphonium chloride, and quaternary phosphonium compounds.

In some embodiments, the process is as follow:

Polyethylene terephthalate is introduced into a reactor. In some embodiments, the reactor is made out of an inert material. In some embodiments, the reactor is made out of stainless steel. In some embodiments, the reactor is made out of high density polyethylene (HDPE).

In some embodiments, polyethylene terephthalate is mixed in with debris, such as, but not limited to bottle cap, glue, paper, residual liquid, dirt, or a combination thereof.

In some embodiments, polyethylene terephthalate is mixed in with other polymers, such as, but not limited to, polyethylene, high density polyethylene, low density polyethylene, polypropylene, or a combination thereof.

A non-polar solvent is added to the polyethylene terephthalate followed by an agent capable of breaking the ester functionality.

In some embodiments, the agent is a mixture of a base and an alcohol. In some embodiments, the agent is a mixture of an acid and an alcohol. In some embodiments, the non-polar solvent and the agent are added simultaneously. In some embodiments, the agent is added prior to the non-polar solvent. In some embodiments, the agent is added after the addition of the non polar solvent.

Upon addition of the agent capable of breaking the ester functionality, the depolymerization of the polyethylene terephthalate starts.

In some embodiments, the reaction is run at atmospheric pressure.

In some embodiments, the reaction is run at ambient temperature.

In some embodiments, the reaction is exothermic. In some embodiments, the reaction is exothermic and the temperature of the reaction mixture rises to at least 30° C., at least 35° C., at least 40° C., at least 45° C., at least 50° C., at least 55° C., or even at least 60° C. However, no external heat sources are used to increase the temperature of the reaction mixture.

In some embodiments, the reaction mixture is stirred. In some embodiments, the reaction mixture is not stirred.

In some embodiments, after completion of the depolymerization reaction, a solid containing terephthalic acid, terephthalic acid salts, terephthalic acid derivatives, unreacted polymers, and debris is obtained. In some embodiments, the terephthalic acid derivatives are terephthalic acid/ethylene glycol oligomers, terephthalic acid ester, or a combination thereof. In some embodiments, the terephthalic acid derivatives are dimethyl terephthalate, 4-(methoxycarbonyl)benzoic acid, or a combination thereof.

In some embodiments, the solids contain a major amount of terephthalic acid salts, a minor amount of terephthalic acid derivatives, unreacted polymers, and debris.

In some embodiments, the solids contain a minor amount of terephthalic acid salts, a major amount of terephthalic acid derivatives, unreacted polymers, and debris.

In some embodiments, the solids do not contain any terephthalic acid salts but only terephthalic acid derivatives, unreacted polymers, and debris. In some embodiments, the terephthalic acid derivatives comprise 4-(methoxycarbonyl)benzoic acid.

In some embodiments, the reaction mixture is filtered to obtain a filter cake and a filtrate. In some embodiments, the reaction mixture is centrifuged to separate the solids from the liquids. In some embodiments, the reaction mixture is purified by liquid/liquid extraction.

In some embodiments, the filter cake obtained is washed with some additional alcohol. In some embodiments, the filter cake obtained is washed with some deionized water.

In some embodiments, the filter cake contains a major amount of 4-(methoxycarbonyl)benzoic acid. In some embodiments, 4-(methoxycarbonyl)benzoic acid is isolated and purified.

In some embodiments, the filter cake obtained is added to an aqueous basic solution. In some embodiments, the filter cake comprises terephthalic acid derivatives. In some embodiments, the terephthalic acid derivatives comprise at least one of terephthalic acid/ethylene glycol oligomers, terephthalic acid mono esters, and terephthalic acid diesters. In some embodiments, the terephthalic acid derivatives are converted to terephthalic acid upon contact with the basic solution. The solution is then filtered to remove non soluble unreacted polymers, non soluble oligomers, and debris. The filtrate obtained contains the solubilized terephthalic acid salts. The pH of the filtrate obtained (either directly or following the basic treatment) is then lowered. In some embodiments, the pH is lowered by addition of an aqueous acid. In some embodiments, the pH is lowered by addition of dry ice. In some embodiments the pH is lowered to 9. In some embodiments the pH is lowered to 8.5. In some embodiments the pH is lowered to 8. In some embodiments the pH is lowered to 7.5. In some embodiments the pH is lowered to 7. In some embodiments the pH is lowered to 6.5. In some embodiments the pH is lowered to 6. In some embodiments the pH is lowered to 5.5. In some embodiments the pH is lowered to 5. In some embodiments the pH is lowered to 4.5. In some embodiments the pH is lowered to 4. In some embodiments the pH is lowered to 3.5. In some embodiments the pH is lowered to 3. In some embodiments the pH is lowered to 2.5. In some embodiments the pH is lowered to 2. In some embodiments the pH is lowered to 1.5. In some embodiments the pH is lowered to 1.

The precipitate is filtered. In some embodiments, the precipitate is washed with some additional alcohol. In some embodiments, the precipitate is washed with some deionized water. The precipitate is then dried.

In some embodiments, the precipitate obtained is pure terephthalic acid. In some embodiments, the precipitate obtained is about 99.9% pure terephthalic acid. In some embodiments, the precipitate obtained is about 99.8% pure terephthalic acid. In some embodiments, the precipitate obtained is about 99.7% pure terephthalic acid. In some embodiments, the precipitate obtained is about 99.6% pure terephthalic acid. In some embodiments, the precipitate obtained is about 99.5% pure terephthalic acid. In some embodiments, the precipitate obtained is about 99.4% pure terephthalic acid. In some embodiments, the precipitate obtained is about 99.3% pure terephthalic acid. In some embodiments, the precipitate obtained is about 99.2% pure terephthalic acid. In some embodiments, the precipitate obtained is about 99.1% pure terephthalic acid. In some embodiments, the precipitate obtained is about 99.0% pure terephthalic acid. In some embodiments, the precipitate obtained is about 98.9% pure terephthalic acid. In some embodiments, the precipitate obtained is about 98.8% pure terephthalic acid. In some embodiments, the precipitate obtained is about 98.7% pure terephthalic acid. In some embodiments, the precipitate obtained is about 98.6% pure terephthalic acid. In some embodiments, the precipitate obtained is about 98.5% pure terephthalic acid. In some embodiments, the precipitate obtained is about 98.4% pure terephthalic acid. In some embodiments, the precipitate obtained is about 98.3% pure terephthalic acid. In some embodiments, the precipitate obtained is about 98.2% pure terephthalic acid. In some embodiments, the precipitate obtained is about 98.1% pure terephthalic acid. In some embodiments, the precipitate obtained is about 98.0% pure terephthalic acid.

The filtrate comprising the alcohol solvent and non polar solvent is collected in a container.

In some embodiments, the filtrate comprises at least one of ethylene glycol, ethylene glycol derivatives, the alcoholic solvent, solubilized terephthatic acid, and soluble impurities. In some embodiments, the soluble impurities are catalysts, inhibitors, stabilizers, pigments, or residual food that were present in the starting polyethylene terephthalate.

The filtrate is distilled. In some embodiments, the distillation is done at atmospheric pressure (about 14 psi) or under pressure (up to about 0.4 psi). In some embodiments, the distillation is performed with increased temperature. In some embodiments, the distillation temperature is less than about 100° C. In some embodiments, the distillate comprises the non polar solvent, the alcohol solvent, traces ethylene glycol, traces water, and traces ethylene glycol derivatives.

In some embodiments, the distillate comprising the non-polar solvent and the alcohol solvent is reused in the first step of the depolymerization process of the present invention. In some embodiments, additional amounts of non-polar solvent and alcohol solvent are added.

In some embodiments, the residue remaining after the distillation comprises ethylene glycol, ethylene glycol derivatives, and non-volatile impurities. In some embodiments, the non-volatile impurities are solids. In some embodiments, the non-volatile impurities are filtered off.

The filtate comprises ethylene glycol and ethylene glycol derivatives.

In some embodiments, the ethylene glycol is purified by distillation. In some embodiments, the distillation is done at atmospheric pressure (about 14 psi) or under pressure (up to about 0.4 psi). In some embodiments, the distillation is performed with increased temperature. In some embodiments, the distillation temperature is less than about 250° C.

In some embodiments, the ethylene glycol is purified by ceramic membrane filtration.

In some embodiments, the ethylene glycol is about 99.9% pure. In some embodiments, the ethylene glycol is about 99.8% pure. In some embodiments, the ethylene glycol is about 99.7% pure. In some embodiments, the ethylene glycol is about 99.6% pure. In some embodiments, the ethylene glycol is about 99.5% pure. In some embodiments, the ethylene glycol is about 99.4% pure. In some embodiments, the ethylene glycol is about 99.3% pure. In some embodiments, the ethylene glycol is about 99.2% pure. In some embodiments, the ethylene glycol is about 99.1% pure. In some embodiments, the ethylene glycol is about 99.0% pure. In some embodiments, the ethylene glycol is about 98.9% pure. In some embodiments, the ethylene glycol is about 98.8% pure. In some embodiments, the ethylene glycol is about 98.7% pure. In some embodiments, the ethylene glycol is about 98.6% pure. In some embodiments, the ethylene glycol is about 98.5% pure. In some embodiments, the ethylene glycol is about 98.4% pure. In some embodiments, the ethylene glycol is about 98.3% pure. In some embodiments, the ethylene glycol is about 98.2% pure. In some embodiments, the ethylene glycol is about 98.1% pure. In some embodiments, the ethylene glycol is about 98.0% pure.

Certain Terminology

The section headings used herein are for organizational purposes only and are not to be construed as limiting the subject matter described.

Unless defined otherwise, all technical and scientific terms used herein have the same meaning as is commonly understood to which the claimed subject matter belongs. In the event that there are a plurality of definitions for terms herein, those in this section prevail.

It is to be understood that the general description and the detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used herein, the term "about" or "approximately" means within 20%, preferably within 10%, and more preferably within 5% of a given value or range.

As used herein, ambient temperature is a colloquial expression for the typical or preferred indoor (climate-controlled) temperature to which people are generally accustomed. It represents the small range of temperatures at which the air feels neither hot nor cold, approximately 21° C. In some embodiments, ambient temperature is 25±5° C. In some embodiments, ambient temperature is 18° C. In some embodiments, ambient temperature is 19° C. In some embodiments, ambient temperature is 20° C. In some embodiments, ambient temperature is 21° C. In some embodiments, ambient temperature is 22° C. In some embodiments, ambient temperature is 23° C. In some embodiments, ambient temperature is 24° C. In some embodiments, ambient temperature is 25° C. In some embodiments, ambient temperature is 26° C. In some embodiments, ambient temperature is 27° C. In some embodiments, ambient temperature is 28° C. In some embodiments, ambient temperature is 29° C. In some embodiments, ambient temperature is 30° C. In some embodiments, ambient temperature is 31° C. In some embodiments, ambient temperature is 32° C.

As used in this specification and the appended claims, depolymerization, refer to a way of breaking down a polymer to its starting material. It is essentially the opposite of polymerization. In some embodiments, the depolymerization is achieved by glycolysis, methanolysis or hydrolysis, categorized by the depolymerization reactant used, such as glycol, methanol or water, respectively.

Definition of standard chemistry terms may be found in reference works, including but not limited to, Carey and Sundberg "Advanced Organic Chemistry 4$^{th}$ Ed." Vols. A (2000) and B (2001), Plenum Press, New York.

The terms below, as used herein, have the following meanings, unless indicated otherwise:

"Linear alkyl" refers to a straight hydrocarbon chain radical which is attached to the rest of the molecule by a single bond. A linear alkyl comprising up to 4 carbon atoms is referred to as a linear $C_1$-$C_4$ alkyl, likewise, for example, a linear alkyl comprising up to 3 carbon atoms is a linear $C_1$-$C_3$ alkyl. Linear alkyl groups include linear $C_1$-$C_4$ alkyl, linear $C_1$-$C_3$ alkyl, linear $C_1$-$C_2$ alkyl, linear $C_2$-$C_3$ alkyl and linear $C_2$-$C_4$ alkyl. Representative alkyl groups include, methyl, ethyl, propyl, and butyl.

"Branched alkyl" refers to a branched hydrocarbon chain radical which is attached to the rest of the molecule by a single bond. A branched alkyl comprising between 3 and 4 carbon atoms is referred to as a branched $C_3$-$C_4$ alkyl. Representative branched alkyl groups include, but are not limited to t-butyl, s-butyl, i-butyl, i-propyl, and s-propyl.

"Cyclic alkyl" refers to a cyclic hydrocarbon chain radical which is attached to the rest of the molecule by a single bond. A cyclic alkyl comprising between 3 and 8 carbon atoms is referred to as a cyclic $C_3$-$C_8$ alkyl. Cyclic alkyl groups include cyclic $C_3$-$C_8$ alkyl, cyclic $C_3$-$C_7$ alkyl, cyclic $C_3$-$C_6$ alkyl, and cyclic $C_3$-$C_4$ alkyl. Representative cyclic alkyl groups include, but are not limited to cyclopropyl, cyclobutyl, cyclopentyl, cyclohexyl, or cycloheptyl.

"Linear $C_1$-$C_4$ alcohol", "branched $C_3$-$C_4$ alcohol", and "cyclic $C_3$-$C_8$ alcohol" refer to the formula ROH where R is an alkyl radical as defined above. Representative alcohol includes, but are not limited to, methanol, ethanol, n-propanol, n-butanol, t-butanol, s-butanol, i-butanol, propanol, s-propanol, cyclopropanol, cyclobutanol, cyclopentanol, cyclohexanol, or cycloheptanol. In some embodiments, the alcohol is methanol. In some embodiments, the alcohol is ethanol.

"$C_1$-$C_4$ Alkoxy" refers to a radical of the formula —OR where R is an alkyl radical as defined having from one to four carbon atoms. Representative alkoxy groups include, but are not limited to, methoxy, ethoxy, n-propoxy, n-butoxy, t-butoxy, s-butoxy, i-butoxy, i-propoxy, and s-propoxy. In some embodiments, the alkoxy is methoxy. In some embodiments, the alkoxy is ethoxy.

EXAMPLES

The following examples are intended to illustrate but not limit the disclosed embodiments.

Example 1

Washed and shredded polyethylene terephthalate (2 Kg, including caps and labels) was introduced in a stainless steel reactor. Dichloromethane (300 mL) was added and the mixture was stirred at ambient temperature and atmospheric pressure. Potassium hydroxide (716 g) dissolved in methanol (6 L) followed by an additional amount of methanol (0.4 L) were then added to the reaction mixture and the resulting mixture was stirred for 66 minutes (aliquots taken at 2, 10, 25, 35, and 50 minutes showed that the depolymerization reaction was complete after 25 minutes). The reaction mixture was then filtered. The filter cake (containing caps, labels, non depolymerized polyethylene terephthalate, trace ethylene glycol, and small amount of the potassium salt of terephthalic acid) was washed with deionized water.

The pH of the filtrate was lowered to about 2 by addition of aqueous sulfuric acid. The precipitate obtained was filtered and washed with a minimum amount of methanol to yield terephthalic acid.

The filtrate was distilled to first recover the dichloromethane and the methanol and then to recover the ethylene glycol.

Example 2

Comparative Example

Experiment #1:
Washed and shredded polyethylene terephthalate (2.5 g, including caps and labels) was added to a solution of potassium hydroxide (10 mL, 5M in methanol) and DMSO (40 mL). The resulting mixture was stirred at ambient temperature and atmospheric pressure for 30 minutes.

Experiment #2:
Washed and shredded polyethylene terephthalate (2.5 g, including caps and labels) was added to a solution of potassium hydroxide (10 mL, 5M in methanol) and dichloromethane (40 mL). The resulting mixture was stirred at ambient temperature and atmospheric pressure for 30 minutes.

After 30 minutes complete depolymerization was achieved in Experiment #2 while the depolymerization in Experiment #1 had barely started. After three days the depolymerization in the Experiment #1 was still not complete.

In the case of Experiment #2, 1.7 g of terephthalic acid was recovered.

Example 3

Washed and shredded polyethylene terephthalate (58 g, including caps and labels) was added to a solution of potassium hydroxide (100 g in methanol) and dichloromethane. The resulting mixture was stirred at atmospheric pressure to yield 40 g of terephthalic acid.

Example 4

Dichloromethane (4.5 Kg) was added to washed and shredded white polyethylene terephthalate without caps or labels (BLT grade, 15 Kg). The mixture was stirred at ambient temperature for 18 minutes followed by addition of a mixture of potassium hydroxide (8.8 Kg) in methanol (30 Kg). The internal temperature was measured to be 50° C. The resulting mixture was stirred for 45 minutes. The impurity profile of the resulting terephthalic acid is shown in table 1.

TABLE 1

| Properties | Results | Units | Method |
|---|---|---|---|
| 4-Carboxybenzaldehyde | 14.4 | ppm | HPLC-MS |
| para-Toluic Acid | 94.4 | ppm | HPLC-MS |
| Al | 0.345 ± 0.004 | ppm | ICP-MS |
| As | under detection limit | ppm | ICP-MS |
| Ca | 4.591 ± 0.021 | ppm | ICP-MS |
| Co | 0.007 ± 0.022 | ppm | ICP-MS |
| Cr | 0.235 ± 0.007 | ppm | ICP-MS |
| Fe | 0.360 ± 0.008 | ppm | ICP-MS |
| K | 180 ± 2.592 | ppm | ICP-MS |
| Mn | 0.014 ± 0.006 | ppm | ICP-MS |
| Mo | 0.009 ± 0.001 | ppm | ICP-MS |
| Na | 126.362 ± 1.364 | ppm | ICP-MS |
| Ni | 0.019 ± 0.001 | ppm | ICP-MS |
| Ti | 0.029 ± 0.001 | ppm | ICP-MS |
| Pb | 0.146 ± 0.002 | ppm | ICP-MS |

Example 5

In a 250 mL pyrex flask was introduced polyethylene terephthalate (10 g) and dichloromethane (6 g). Separately sodium hydroxide (4.32 g) was dissolved in water (3.6 g) and methanol (32.93 g). After 20 min., the basic solution was added to the dichloromethane/PET mixture and the admixing was continued for 10 days at room temperature and atmospheric pressure. Water (200 mL) was added to dissolve all the terephthalic acid salts and the solution was filtered to yield 0.1 g of unreacted starting material or insoluble oligomers. The aqueous solution was acidified and a precipitate formed. The solids were filtered to yield 99% of terephthalic acid and terephthalic acid derivatives.

Example 6

In a 250 mL pyrex flask was introduced polyethylene terephthalate (10 g) and dichloromethane (5 g). Separately sodium hydroxide (2.65 g) and potassium hydroxide (1.5 g) were each dissolved in methanol (50 g). After 20 min., the basic solutions were added to the dichloromethane/PET mixture and the admixing was continued for 3 days at room temperature and atmospheric pressure. Water (200 mL) was added to dissolve all the terephthalic acid salts and terephthalic acid derivatives. The solution was filtered to yield 0.85 g of unreacted starting material or insoluble oligomers. The aqueous solution was acidified and a precipitate formed. The solids were filtered to yield 4.65 g of a mixture of terephthalic acic/4-(methoxycarbonyl)benzoic acid (2.16:1 ratio).

What is claimed is:
1. A process for depolymerizing a polymer comprising an ester functionality, comprising admixing the polymer with a mixture comprising:
  (i) a halogenated solvent selected from the group consisting of dichloromethane, dichloroethane, tetrachloroethane, chloroform, tetrachloromethane, and trichloroethane; and

(ii) a mixture of an alcohol and a hydroxide;
wherein the admixing is continued for a sufficient time to depolymerize at least a portion of the polymer; and
wherein the process is performed without applying external heat.

2. The process of claim 1, wherein the mixture of the alcohol and the hydroxide is added to the polymer simultaneously with the halogenated solvent.

3. The process of claim 1, wherein the ratio of the halogenated solvent to alcohol is about 1:10 to about 1:50 (v:v).

4. The process of claim 1, wherein the polymer is admixed with the halogenated solvent, the hydroxide, and the alcohol for about 0 h to about 5 h.

5. The process of claim 4, wherein the polymer is admixed with the halogenated solvent, the hydroxide, and the alcohol at atmospheric pressure.

6. The process of claim 1, wherein the alcohol is a linear $C_1$-$C_4$ alcohol.

7. The process of claim 1, wherein the hydroxide is selected from the group consisting of an alkali metal hydroxide, an alkaline earth metal hydroxide, an ammonium hydroxide, and a combination thereof.

8. The process of claim 1, wherein the polymer is in the form of waste material.

9. The process of claim 8, wherein the waste material further comprises debris that do not include a polymer comprising an ester functionality.

10. The process of claim 9, wherein the debris comprises at least one of bottle caps, glue, paper, residual liquid, and dirt.

11. The process of claim 1, wherein the polymer comprising an ester functionality is depolymerized to form terephthalic acid or a salt thereof and ethylene glycol.

12. The process of claim 11, wherein the terephthalic acid or salt thereof contains less than about 3% of an impurity (w/w).

13. The process of claim 12, wherein the impurity comprises at least one of isophthalic acid, phthalic acid, 4-methylbenzoic acid, 4-formylbenzoic acid, and metals.

14. A process for depolymerizing of polymer comprising an ester functionality, comprising admixing the polymer with a mixture comprising:
(i) about 3 to about 5% (vol.) of a halogenated solvent selected from the group consisting of dichloromethane, dichloroethane, tetrachloroethane, chloroform, tetrachloromethane, and trichloroethane;
(ii) about 95 to about 97% (vol.) of a linear $C_1$-$C_4$ alcohol; and
(iii) a hydroxide;
wherein the admixing is continued for about 1 h; and
wherein the process is performed without applying external heat.

15. The process of claim 14, wherein the polymer comprising an ester functionality is depolymerized to form terephthalic acid or a salt thereof and ethylene glycol.

16. The process of claim 15, wherein the terephthalic acid or salt thereof contains less than about 3% of an impurity (w/w).

17. The process of claim 16, wherein the impurity comprises at least one of isophthalic acid, phthalic acid, 4-methylbenzoic acid, 4-formylbenzoic acid, and metals.

18. A process for depolymerizing polyethylene terephthalate comprising admixing polyethylene terephthalate with a mixture comprising:
(i) about 3 to about 5% (vol.) of a halogenated solvent selected from the group consisting of dichloromethane, dichloroethane, tetrachloroethane, chloroform, tetrachloromethane, and trichloroethane;
(ii) about 95 to about 97% (vol.) of a linear $C_1$-$C_4$ alcohol; and
(iii) a hydroxide;
wherein the admixing is continued for about 1 h; and
wherein the process is performed at without applying external heat.

* * * * *